(12) United States Patent
Dai et al.

(10) Patent No.: US 6,712,504 B1
(45) Date of Patent: Mar. 30, 2004

(54) METHOD FOR DETERMINING THE RELATIVE HUMIDITY OF A VOLUME OF AIR HAVING A TEMPERATURE OF 100° C OR GREATER

(75) Inventors: Chunping Dai, Vancouver (CA); Guoxing Du, Nanjing (CN)

(73) Assignee: Forintek Canada Corp., Vancouver (CA)

( * ) Notice: Subject to any disclaimer, the term of this patent is extended or adjusted under 35 U.S.C. 154(b) by 0 days.

(21) Appl. No.: 10/260,623

(22) Filed: Oct. 1, 2002

(51) Int. Cl.$^7$ .............................................. G01N 25/56
(52) U.S. Cl. ........................ 374/45; 374/54; 374/141; 73/29.01
(58) Field of Search ............................. 374/16, 28, 45, 374/54, 141; 73/29.01, 29.02, 335.06, 335.08; 702/130, 137, 138

(56) References Cited

U.S. PATENT DOCUMENTS

| | | | | |
|---|---|---|---|---|
| 3,681,992 A | * | 8/1972 | Cofoid et al. | 374/109 |
| 3,890,703 A | | 6/1975 | Plessey | |
| 3,926,052 A | * | 12/1975 | Bechtel | 73/335.05 |
| 4,227,411 A | * | 10/1980 | Abramovich | 73/335.02 |
| 4,408,482 A | * | 10/1983 | Zhuravlev et al. | 73/75 |
| H000381 H | * | 12/1987 | Pounds et al. | 374/142 |
| 5,148,710 A | * | 9/1992 | Gudehus et al. | 73/335.06 |
| 5,165,793 A | * | 11/1992 | Rall et al. | 374/28 |
| 5,168,754 A | * | 12/1992 | Erbs | 73/335.02 |
| 5,435,146 A | * | 7/1995 | Clark | 62/126 |
| 5,485,747 A | * | 1/1996 | Antikainen et al. | 73/335.03 |
| 6,229,318 B1 | | 1/1998 | Suda | |
| 5,816,704 A | * | 10/1998 | Campbell et al. | 374/28 |
| 6,073,480 A | * | 6/2000 | Gokhfeld | 73/29.02 |
| 6,299,147 B1 | * | 10/2001 | Mitter | 261/128 |

OTHER PUBLICATIONS

NGK Spark Plug Co. Ltd., High temperature humidity sensor using a limiting current type plane oxygen sensor, J. Ceram. Soc. Jpn., Mar. 1992, pp. 282–286, vol. 100, No. 3, Jpn (abstract only).

High temperature humidity sensor, Key Engineering Materials, Conference and exhibition of European Ceramic Society, Jul. 1, 2002, vol. 206–213, No, pt. 2, Switzerland (abstract only).

Abstract of JP 07021121, filed Jan. 13, 1995, published as JP 08145932 on Jun. 7, 1996.

\* cited by examiner

Primary Examiner—Diego Gutierrez
Assistant Examiner—Lydia M. De Jesús
(74) Attorney, Agent, or Firm—Oyen Wiggs Green & Mutala

(57) ABSTRACT

A method for determining the relative humidity of a volume V of air having a temperature of 100° C. or greater. The method comprises the steps of measuring the temperature $T_V$ of the volume of air and determining from that temperature the saturation vapor pressure $p_{sat(V)}$ of the volume of air; collecting from the volume of air a sample volume S of air and cooling it to a temperature $T_S$ below 100° C., but above the dew point of the sample volume of air; determining from the temperature $T_S$ the saturation vapor pressure $p_{sat(S)}$ of the cooled sample volume of air; determining the relative humidity $RH_S$ of the sample volume of air from $T_S$ and from the wet bulb temperature of the sample of air; and performing the calculation $$RH_V = RH_S \times p_{sat(S)}/p_{sat(V)}$$

to obtain a relative humidity $RH_V$ of the volume of air.

5 Claims, 2 Drawing Sheets

TABLE 1. Saturation vapour pressure (e°(T)) for different temperatures (T)

| T °C | e$_s$ kPa | T °C | e°(T) kPa | T °C | e°(T) kPa | T °C | e$_s$ kPa |
|---|---|---|---|---|---|---|---|
| 1.0 | 0.657 | 13.0 | 1.498 | 25.0 | 3.168 | 37.0 | 6.275 |
| 1.5 | 0.681 | 13.5 | 1.547 | 25.5 | 3.263 | 37.5 | 6.448 |
| 2.0 | 0.706 | 14.0 | 1.599 | 26.0 | 3.361 | 38.0 | 6.625 |
| 2.5 | 0.731 | 14.5 | 1.651 | 26.5 | 3.462 | 38.5 | 6.806 |
| 3.0 | 0.758 | 15.0 | 1.705 | 27.0 | 3.565 | 39.0 | 6.991 |
| 3.5 | 0.785 | 15.5 | 1.761 | 27.5 | 3.671 | 39.5 | 7.181 |
| 4.0 | 0.813 | 16.0 | 1.818 | 28.0 | 3.780 | 40.0 | 7.376 |
| 4.5 | 0.842 | 16.5 | 1.877 | 28.5 | 3.891 | 40.5 | 7.574 |
| 5.0 | 0.872 | 17.0 | 1.938 | 29.0 | 4.006 | 41.0 | 7.778 |
| 5.5 | 0.903 | 17.5 | 2.000 | 29.5 | 4.123 | 41.5 | 7.986 |
| 6.0 | 0.935 | 18.0 | 2.064 | 30.0 | 4.243 | 42.0 | 8.199 |
| 6.5 | 0.968 | 18.5 | 2.130 | 30.5 | 4.366 | 42.5 | 8.417 |
| 7.0 | 1.002 | 19.0 | 2.197 | 31.0 | 4.493 | 43.0 | 8.640 |
| 7.5 | 1.037 | 19.5 | 2.267 | 31.5 | 4.622 | 43.5 | 8.867 |
| 8.0 | 1.073 | 20.0 | 2.338 | 32.0 | 4.755 | 44.0 | 9.101 |
| 8.5 | 1.110 | 20.5 | 2.412 | 32.5 | 4.891 | 44.5 | 9.339 |
| 9.0 | 1.148 | 21.0 | 2.487 | 33.0 | 5.030 | 45.0 | 9.582 |
| 9.5 | 1.187 | 21.5 | 2.564 | 33.5 | 5.173 | 45.5 | 9.832 |
| 10.0 | 1.228 | 22.0 | 2.644 | 34.0 | 5.319 | 46.0 | 10.086 |
| 10.5 | 1.270 | 22.5 | 2.726 | 34.5 | 5.469 | 46.5 | 10.347 |
| 11.0 | 1.313 | 23.0 | 2.809 | 35.0 | 5.623 | 47.0 | 10.613 |
| 11.5 | 1.357 | 23.5 | 2.896 | 35.5 | 5.780 | 47.5 | 10.885 |
| 12.0 | 1.403 | 24.0 | 2.984 | 36.0 | 5.941 | 48.0 | 11.163 |
| 12.5 | 1.449 | 24.5 | 3.075 | 36.5 | 6.106 | 48.5 | 11.447 |

FIGURE 2

METHOD FOR DETERMINING THE RELATIVE HUMIDITY OF A VOLUME OF AIR HAVING A TEMPERATURE OF 100° C OR GREATER

TECHNICAL FIELD

The present invention relates to methods for determining the relative humidity of volumes of air, and in particular to methods for determining the relative humidity of a volume of hot air enclosed within industrial machinery such as veneer dryers and the like.

BACKGROUND

Wood is often peeled, sawn, or sliced into sheets of a certain thickness which are combined with adhesive resins to form wood products such as plywood. These wood sheets or "veneer" sheets are formed in veneer mills and are generally dried in veneer dryers before being adhered to one another.

Plywood veneer dryers are large, heated enclosures through which veneer sheets are transported along a conveyor system. A typical veneer dryer might be 80–100 feet in length. A typical drying temperature in a veneer dryer might be 200° C. In these veneer dryers, air is circulated by large fans to remove moisture from the veneer sheets.

These veneer dryers dry wet veneer to an average moisture content that is compatible with the adhesive system being used to bond the veneers. This moisture content is also somewhat dependent upon the end product being manufactured. Plywood, for example, is generally manufactured from veneers having a moisture content of between 3%–8% moisture content by dry weight. The veneers cannot be properly bonded unless they have the correct moisture content.

Given the importance of the moisture content of the veneers, then, it is important to monitor and control the moisture content of the veneers in the dryers. Moisture content can generally be controlled by controlling the temperature of the dryer, the length of time the veneers are allowed to be dried, and the relative humidity of the air within the dryers.

The relative humidity of the air within a veneer dryer is generally controlled by venting hot, humid air from the dryer and replacing it with fresh, cool air. However, venting the hot air from the dryer causes energy losses, and it is desirable to closely monitor the relative humidity so as not to unnecessarily vent an excessive amount of hot air.

To this point in time there has not been developed a suitable, cost effective system and method for determining and monitoring the relative humidity within a veneer dryer.

It is quite common and well known to monitor relative humidity within a lumber kiln using the dry and wet bulb method, which will be very familiar to those with knowledge of wood drying and with psychrometry generally. The relative humidity within a lumber kiln can be determined by obtaining the dry bulb temperature and the wet bulb temperature within the kiln and by thereafter referring to a reference table or a database for the relative humidity given these two temperatures. However, it is well known that the dry and wet bulb method of determining relative humidity cannot be suitably relied upon to provide accurate determinations of relative humidity when the temperature of the air exceeds 100° C. (the boiling point of water), as it does in a veneer dryer, since proper wet bulb temperatures cannot be obtained.

Accordingly, relative humidity has not typically been determined in veneer dryers by the dry and wet bulb method. Rather, various expensive and complicated optical and electrical systems have been suggested and employed. Other systems (such as the "Zirconia Oxygen Analyzer") measure oxygen content directly and humidity indirectly, but these systems do not provide accurate readings in atmospheric environments like those within a veneer dryer wherein the "fresh" air has been contaminated by organic compounds given off by the drying wood, and by byproducts of the combustion of fuels (such as natural gas) used to heat the air within the veneer dryer. So, these oxygen-measuring systems, as expensive as they might be, do not provide very accurate readings within a veneer dryer.

There accordingly remains a need for a relatively simple, inexpensive method for determining the relative humidity of a volume of hot air enclosed within a veneer dryer.

SUMMARY OF INVENTION

The present invention provides a method for determining the relative humidity of a volume of air having a temperature of 100° C. or greater. The method comprises the steps of:

measuring the temperature $T_V$ of the volume of air;

determining from $T_V$ the saturation vapor pressure $p_{sat(V)}$ of the volume of air;

collecting from the volume of air a sample volume of air;

cooling the sample volume of air to a temperature $T_S$ below 100° C., but above the dew point of the sample volume of air;

determining from $T_S$ the saturation vapor pressure $p_{sat(S)}$ of the cooled sample volume of air;

determining the relative humidity $RH_S$ of the sample volume of air; and performing the calculation $$RH_V = RH_S \times p_{sat(S)}/p_{sat(V)}$$

to obtain a relative humidity $RH_V$ of the volume of air.

In a preferred embodiment, the step of determining the relative humidity $RH_S$ of the sample volume of air comprises considering the temperature $T_S$ to be the dry bulb temperature of the sample volume of air, and further comprises measuring the wet bulb temperature of the sample volume of air. With these dry and wet bulb temperatures, the relative humidity $RH_S$ may be obtained from a reference source.

In a further preferred embodiment of the invention, the method is carried out within a veneer drying system and the relative humidity of the volume of air calculated is that of the air within the dryer. The sample of air removed from the dryer may be returned to the dryer after the calculation of relative humidity is performed.

BRIEF DESCRIPTION OF DRAWINGS

In the accompanying drawings which illustrate specific embodiments of the invention, but which should not be construed as restricting the spirit or scope of the invention in any way:

FIG. 2 is a table showing saturation vapor pressure (e(T)) for different temperatures (T).

DESCRIPTION

Figure 1:
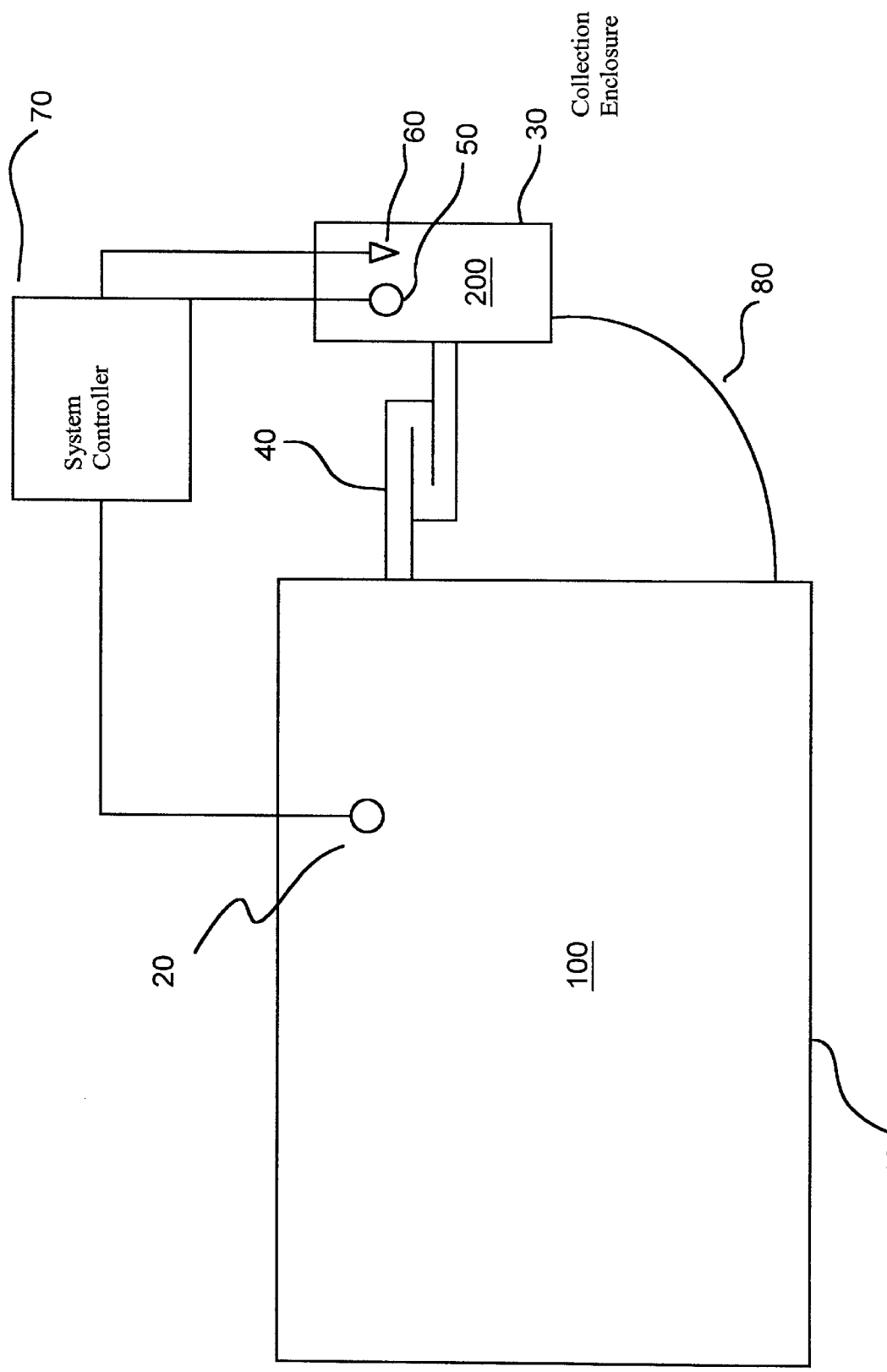
FIG. 1 is schematic view of a veneer drying system employing the method of the present invention.

Throughout the following description, specific details are set forth in order to provide a more thorough understanding of the invention. However, the invention may be practised without these particulars. In other instances, well known elements have not been shown or described in detail to avoid unnecessarily obscuring the invention. Accordingly, the specification and drawings are to be regarded in an illustrative, rather than a restrictive, sense.

The inventors foresee the method of the present invention being carried out in many circumstances wherein it is desired to determine the relative humidity of a volume of air having a temperature (or "dry bulb" temperature) of 100° C. or greater. The inventors are particularly interested in monitoring relative humidity within veneer dryers, and thus it is such a system which is illustrated and described herein. However, it should be understood that the references herein to veneer dryers are for illustrative purposes only, and that the presently-described system and method will have application in other circumstances and situations.

Accordingly, referring to FIG. 1, in a system wherein it is desired to determine the relative humidity of a volume of hot air, such as within an enclosure like a veneer dryer 10, the present method provides that the temperature $T_V$ of the volume of air 100 within the dryer 10 be measured. This can suitably be accomplished with a temperature sensor such as dry bulb temperature sensor 20. The air 100 within dryer 10 typically has, as described above, a temperature significantly greater than 100° C. "Air" as described herein, refers generally to the various gases within dryer 10.

As is well known to those in the art of psychrometry, air at a given temperature has a fixed saturation vapor pressure. As known in the art, this pressure can be determined from any number of reference sources, such as the following, all of which are incorporated herein by reference:

List, Robert J. Smithsonian Meteorological Tables. Smithsonian Institution Press, City of Washington Allen, Richard G. et al. 1998. Crop evapotranspiration—Guidelines for computing crop water requirements—FAO Irrigation and drainage paper 56. Food and Agriculture Organization of the United Nations Harrison, L. D. 1965. Fundamental concepts and definitions relating to humidity. Humidity and Moisture (A. Wexler, ed), Meas. Contr. Sci. Ind. 3:3–70

Jensen, M. E., R. D. Burman, and R. G. Allen. 1990. Evapotranspiration and irrigation water requirements. ASCE Manuals and Reports on Engineering Practice No. 70.

Murray, F. W. 1967. On the computation of saturation vapor pressure. J. App. Meteor. 6:203–204.

Rosenberg, N. J., B. L. Blad, and S. B. Verma. 1990. Microclimate. Second edition. John Wiley & Sons, New York FIG. 2 shows a partial table of saturation vapor pressures for given temperatures.

A further step in the present method provides, after obtaining temperature $T_V$, that the saturation vapor pressure $p_{sat(V)}$ of the air within the dryer 10 be determined from a reference in this fashion, knowing $T_V$.

The present method also provides the step of collecting a sample volume of air 200 from dryer 10. This can be accomplished in a dryer system by pumping a relatively small volume of air 200 from dryer 10 by a fan to a collection enclosure 30 remote from dryer 10. The collected sample volume of air 200 is cooled, and may be efficiently cooled by running it through cooling conduit 40.

The air 200 is cooled to a temperature $T_S$ below 100° C., but air 200 is not allowed to cool to such an extent that condensation occurs. In other words, the air 200 is not cooled to its dew point. Temperature $T_S$ may be measured by means of dry bulb temperature sensor 50. Other temperature sensors (not shown) may be placed within conduit 40 to control the amount of cooling of air 200, so that temperature $T_S$ indeed ends up to be below 100° C. once air 200 is within enclosure 30.

In a subsequent step of the present method, the saturation vapor pressure $p_{sat(S)}$ of the sample volume of air 200 is determined from $T_S$, as described earlier by referring to well known references. Before or after this particular step, but after air 200 has been cooled, the wet bulb temperature of air 200 within enclosure 30 is determined using a wet bulb temperature sensor 60. Of course, the wet bulb temperature of air 200 must be determined at the same time $T_S$ is determined, or at least, while $T_S$ remains constant.

As is well known in the art, at any particular temperature, the relative humidity of air (RH) can be determined by the following calculation:

$$RH = p/p_{sat}$$

where RH is relative humidity, p is the partial water vapor pressure in the air, and $p_{sat}$ is the saturation water vapor pressure of the air.

Given this relationship, the relative humidity of cooled air 200 can be expressed as follows:

$$RH_S = p_S/p_{sat(S)}$$

where $RH_S$ is relative humidity of sample air 200, $p_S$ is the partial water vapor pressure in the air 200, and $p_{sat(S)}$ is the saturation water vapor pressure of sample air 200.

Further, the relative humidity of hot air 100 can be expressed as follows:

$$RH_V = p_V/p_{sat(V)}$$

where $RH_V$ is relative humidity of air 100, $p_V$ is the partial water vapor pressure in the air 100, and $p_{sat(V)}$ is the saturation water vapor pressure of the air 100.

The ratio of $RH_S$ / $RH_V$ can be expressed as follows:

$$p_S \times p_{sat(V)} / p_V \times p_{sat(S)}$$

Since the absolute humidity does not change before or after cooling, if condensation is not permitted to occur, $p_S = p_V$, and $$RH_S/RH_V = p_{sat(V)}/p_{sat(S)}$$

Thus, $RH_V = RH_S \times p_{sat(S)}/p_{sat(V)}$

Accordingly, knowing $RH_S$, $p_{sat(S)}$ and $p_{sat(V)}$, the relative humidity $RH_V$ within a veneer dryer can be calculated.

The various steps in the method might be summarized as follows, then:

a) measuring the temperature $T_V$ of a volume of air;

b) determining from the temperature $T_V$ the saturation vapor pressure $p_{sat(V)}$ of the volume of air;

c) collecting from the volume of air a sample volume S of air;

d) cooling the sample volume of air to a temperature $T_S$ below 100° C., but above the dew point of the sample volume of air;

e) determining from the temperature $T_S$ the saturation vapor pressure $p_{sat(S)}$ of the cooled sample volume of air;

f) determining the relative humidity $RH_S$ of the sample volume of air by measuring the wet bulb temperature of the sample volume of air and determining the relative humidity from the temperature $T_S$ and from the wet bulb temperature; and g) performing the calculation $$RH_V = RH_S \times p_{sat(S)}/p_{sat(V)}$$

to obtain a relative humidity $RH_V$ of said volume of air.

It should be clear that while certain of these steps must follow others, some can be performed in an order other than indicated above. For example, it will be understood that steps "f" can precede step "e". What is essential that the relative humidity of the sample of air, and the saturation pressures of the volume of air and of the sample of air be determined, so that the calculation of step "g" can be performed.

EXAMPLE

The hot air dry temperature is measured in a veneer dryer at 135° C. A "wet bulb" temperature measurement taken in the dryer would read 45° C., but this is not accurate for the purpose of determining relative humidity due to th high temperature, as discussed above. A sample of air is collected from the dryer and cooled to a dry temperature of 75.8° C. When cooled to this temperature, a wet temperature is able to be taken, and it is determined to be 33.1° C. From these dry and wet temperatures, the relative humidity of the cooled sample of air is determined to be 6.81%. The saturation water vapor pressure at 75.8° C. is known or determined to be 0.4005 bars. The saturation water vapor pressure at 135° C. known to be 3.145 bars, so the relative humidity of the volume of air in the dryer can be calculated to be:

$$RH_v = 6.81\% \times .4006/3.145$$
$$= 0.868\%$$

The inventors foresee the use of the method in a continuously-operating feedback system such as that shown in FIG. 1, wherein the air 200 is continuously collected from dryer 10, and sampled. Air 200 may be returned to dryer 10 by conduit 80 (rather than merely vented to the atmosphere). In this system, controller 70 continuously monitors relative humidity of the air within the dryer 10 and makes venting adjustments as required.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method for determining the relative humidity of a volume V of air having a temperature of 100° C. or greater, said method comprising the steps of:

a) measuring the temperature $T_V$ of said volume of air;

b) determining from said temperature $T_V$ the saturation vapor pressure $p_{sat(V)}$ of said volume of air;

c) collecting from said volume of air a sample volume S of air;

d) cooling said sample volume of air to a temperature $T_S$ below 100° C., but above the dew point of said sample volume of air;

e) determining from said temperature $T_S$ the saturation vapor pressure $p_{sat(S)}$ of said cooled sample volume of air;

f) determining the relative humidity $RH_S$ of said sample volume of air; and g) performing the calculation $$RH_V = RH_S \times p_{sat(S)}/p_{sat(V)}$$

to obtain a relative humidity $RH_V$ of said volume of air.

2. The method of claim 1 wherein the step of determining the relative humidity $RH_S$ of said sample volume of air comprises measuring the wet bulb temperature of said sample volume of air and determining said relative humidity from said temperature $T_S$ and from said wet bulb temperature.

3. The method of claim 2 further comprising the final step of returning said sample volume of air to said volume of air.

4. The method of claim 2 further comprising the final step of venting said sample volume of air to the atmosphere.

5. The method of claim 1, wherein said method is used to determine the relative humidity of the air within a wood veneer dryer.

* * * * *